United States Patent [19]

Kim et al.

[11] Patent Number: 5,053,572
[45] Date of Patent: Oct. 1, 1991

[54] MULTISTAGE ETHYLBENZENE DEHYDROGENATION PROCESS WITH SPLIT-FLOW HYDROCARBON FEED

[75] Inventors: Dae K. Kim, Naperville; George M. Longland, Jr., Wheaton, both of Ill.

[73] Assignee: Amoco Corporation, Chicago, Ill.

[21] Appl. No.: 584,475

[22] Filed: Sep. 18, 1990

Related U.S. Application Data

[63] Continuation of Ser. No. 350,572, May 11, 1989, abandoned.

[51] Int. Cl.$^5$ .............................................. C07C 4/02
[52] U.S. Cl. .................................... 585/441; 585/440
[58] Field of Search ................................ 585/440, 441

[56] References Cited

U.S. PATENT DOCUMENTS

| | | | |
|---|---|---|---|
| 3,330,087 | 7/1967 | Huckins et al. | 260/669 |
| 3,402,212 | 9/1968 | Gantt | 260/669 |
| 3,855,330 | 12/1974 | Mendelsohn et al. | 260/669 R |
| 4,347,396 | 8/1982 | Takano et al. | 585/441 |

FOREIGN PATENT DOCUMENTS 6135427  10/1981  Japan .

Primary Examiner—Patrick P. Garvin
Assistant Examiner—E. D. Irzinski
Attorney, Agent, or Firm—Robert G. Ladd; William H. Magidson; Ralph C. Medhurst

[57] ABSTRACT

An improved multistage ethylbenzene dehydrogenation process comprising feeding steam and a major fraction of a hydrocarbon feed to a first reactor and feeding a remaining minor fraction of the hydrocarbon feed and a product of the first reactor to a second reactor.

16 Claims, 1 Drawing Sheet

MULTISTAGE ETHYLBENZENE DEHYDROGENATION PROCESS WITH SPLIT-FLOW HYDROCARBON FEED

This is a continuation of application Ser. No. 350,572, filed May 11, 1989, now abandoned.

FIELD OF THE INVENTION

This invention relates to an improved process for the vapor phase catalytic dehydrogenation of alkylated aromatic hydrocarbons to produce vinyl-substituted aromatic hydrocarbons. More specifically, this invention relates to a multistage ethylbenzene dehydrogenation process in which steam and a major fraction of a hydrocarbon feed is fed to a first stage and a remaining fraction of the hydrocarbon feed and reaction product of the first stage are fed to a second stage.

BACKGROUND OF THE INVENTION

Prior art methods for producing styrene are generally carried out by passing a mixture of ethylbenzene and steam over a fixed bed of dehydrogenation catalyst. In order to heat the reactants to reaction temperature, it is also general practice to admix the ethylbenzene, which is at a temperature significantly below reaction temperature, with steam which has been superheated to a temperature above the reaction temperature so that the mixture is at reaction temperature as it passes over the dehydrogenation catalyst. Since the basic chemical reaction involved, namely the dehydrogenation of ethylbenzene to styrene, is endothermic, there is a significant decrease in the reaction zone temperature as the reaction proceeds. It is not unusual in these prior art processes to witness a drop of perhaps 50° C. to 100° C. within the reaction zone. Naturally, as the temperature decreases, the rapidity of the reaction also decreases so that the overall efficiency of the process declines to a point where it would be economically unattractive unless processing means were found to overcome this disadvantage.

The prior art attempted to solve this problem by drastically increasing the temperature of the superheated steam so that the difference between the inlet temperature of the reactants and the outlet temperature of the reaction products averaged generally the required reaction temperature. However, it was noted that at the instant the superheated steam is admixed with the ethylbenzene, the ethylbenzene undergoes decomposition or cracking through the pyrolytic reaction. In many instances, such pyrolysis is effected to such a degree that the process becomes uneconomical due to the loss of ethylbenzene to carbon monoxide, carbon dioxide, polymeric materials, tars, etc. Another disadvantage is involved with the utility costs in raising the temperature of large quantities of steam to a level far above that required for effecting the dehydrogenation of the ethylbenzene. Additionally, in spite of all these efforts to control the reaction, the conversion of ethylbenzene to styrene remained at approximately the 30 to 40 percent conversion level.

More recently, the prior art has suggested means for increasing the level of conversion by utilizing various schemes for admixing ethylbenzene and steam in such a way as to avoid the pyrolytic reaction. One method has been to split the steam into several portions whereby additional steam is added between catalytic zones in order to reheat the reactants to reaction temperature. In these latter processes, conversions as high as 50% for ethylbenzene to styrene are alleged. However, these latter process schemes do not indicate the method by which the steam and ethylbenzene are heated with the result that utility costs are still prohibitively high for the achievement of the increased conversion level.

U.S. Pat. No. 3,402,212 discloses a method in which steam and hydrocarbons are heated to reaction temperature and maintained thereat in such a fashion that the conversion of ethylbenzene to styrene per pass exceeds 50 weight percent and requires no more than 5 pounds of steam per pound by styrene produced.

U.S. Pat. No. 3,330,878 discloses an improved process for the preparation of styrene from ethylbenzene using at least two dehydrogenation reactors with an intermediate indirect heating step.

U.S. Pat. No. 3,855,330 discloses a process which reportedly could lead to styrene yields of more than 70% in a single reactor by disposing a layer of an oxidation catalyst downstream of a dehydrogenation catalyst layer for combusting hydrogen formed in the reaction without affecting the hydrocarbons present. The oxidation catalyst layer is followed by a second layer of dehydrogenation catalyst.

However, these prior art processes do not indicate the method by which high temperature steam and a major fraction of a hydrocarbon feed mixture containing a minor amount of steam are introduced to the first stage of a multistage dehydrogenation process containing more than two stages and the remaining minor fraction of hydrocarbon feed mixture is admixed with the reaction product of the first stage and fed to the second stage of the process.

Accordingly, it is an object of this invention to provide for an endothermic vapor phase catalytic conversion of hydrocarbons in a multistage dehydrogenation process.

It is another object of this invention to provide a process for the dehydrogenation of ethylbenzene to styrene characterized by high conversion per pass of ethylbenzene to styrene, high purity of recovered styrene and low decline of ethylbenzene conversion over the course of a production run.

It is another object of this invention to effect a more economical method of dehydrogenating ethylbenzene to produce styrene in high conversion and purity.

It is a specific object of this invention to provide an improved multistage ethylbenzene dehydrogenation process in which steam and a major fraction of a hydrocarbon feed is fed to a first stage and a remaining fraction of the hydrocarbon feed and reaction product of the first stage are fed to a second stage.

SUMMARY OF THE INVENTION

An improved multistage ethylbenzene dehydrogenation process comprising feeding steam and a major fraction of an alkyl aromatic hydrocarbon feed to a first reactor and feeding a remaining minor fraction of the alkyl aromatic hydrocarbon feed and a product of the first reactor to a second reactor.

BRIEF DESCRIPTION OF THE INVENTION

Figure 1:
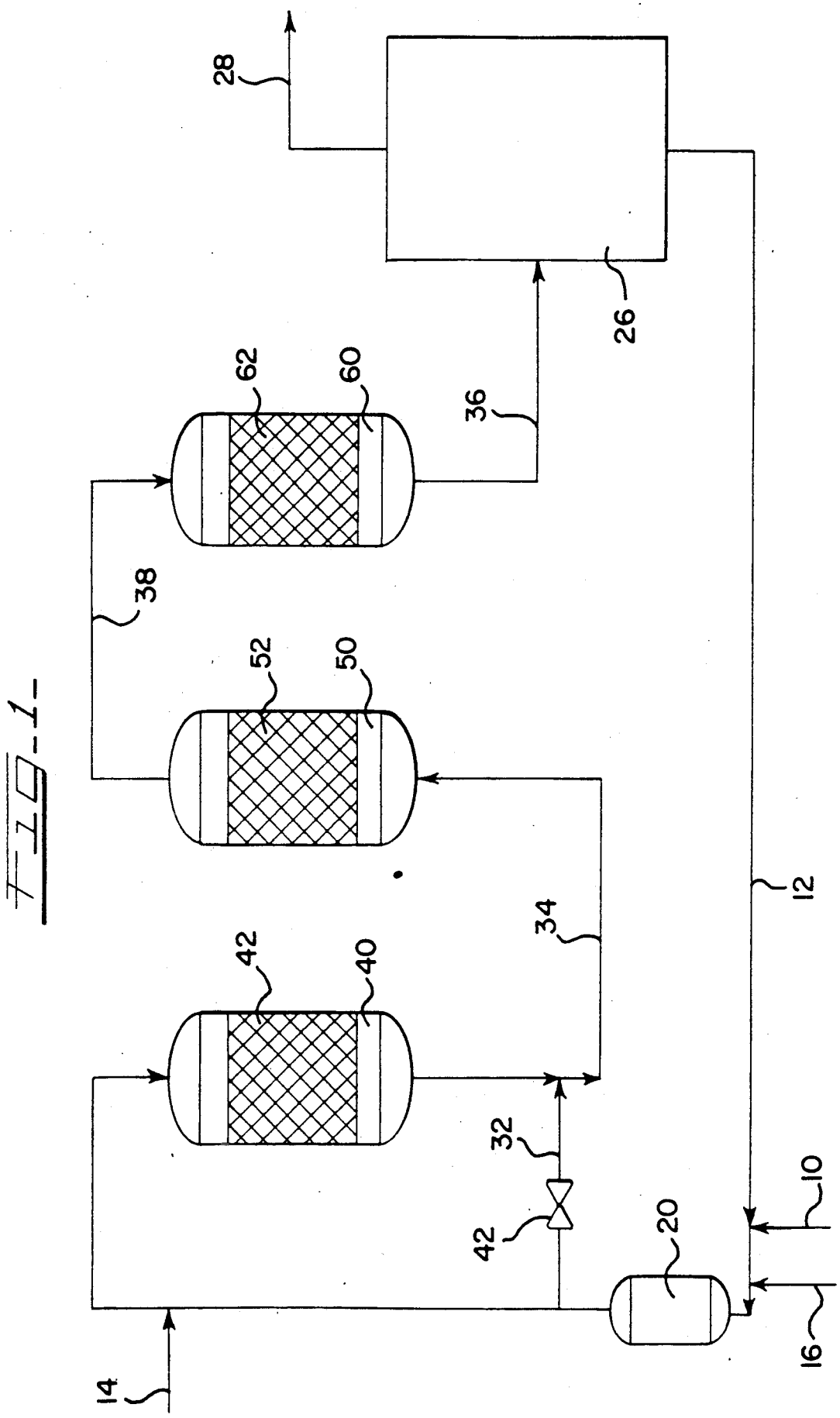
FIG. 1 represents a schematic drawing of the multistage ethylbenzene dehydrogenation process with a split-flow alkyl aromatic hydrocarbon feed.

The invention described herein is a multistage dehydrogenation process for converting ethylbenzene to styrene with improved conversion of ethylbenzene to styrene. In one aspect of this invention multiple dehydrogenation reactors are used in which steam and a major fraction of an alkyl aromatic hydrocarbon feed are introduced to a first dehydrogenation reactor and a dehydrogenation product of the first reactor is combined with the remaining minor fraction of alkyl aromatic hydrocarbon feed and introduced to a second dehydrogenation reactor.

Because of the high temperatures required at the inlet of each catalyst bed, vaporized ethylbenzene is mixed with superheated steam. The steam has several contributions to the catalytically endothermic dehydrogenation reaction of ethylbenzene to styrene including: supplying the heat required to maintain the endothermic reaction, minimizing the amount of coke deposited on the catalyst through the water-gas-shift reaction, reducing the hydrocarbon partial pressure thereby shifting the reaction equilibrium towards the formation of styrene, and contributing significantly to the cost of production.

Dehydrogenation of ethylbenzene to styrene is an energy-intensive process, and therefore, savings in energy usage correspond to significant improvements in process economics. Increased ethylbenzene (EB) conversion reduces the recycle rate of EB, thereby reducing the utility requirements in both the reaction section and the distillation section.

The conversion becomes further limited as the catalyst ages due to deactivation coupled with relatively rapid pressure buildup rates in the catalyst beds which is difficult to alleviate under subatmospheric conditions.

Depending on the age of the catalyst typical EB conversions achieved per pass in a two stage dehydrogenation process are about 60-70 wt.%. The unreacted EB is separated in the distillation section of the styrene recovery system and recycled back to the dehydrogenation reactors. As the dehydrogenation catalyst ages the conversion of EB per pass decreases and the energy consumption per pound of styrene produced increases because of the increased amount of recycled EB.

By adding a third reactor significant increases of about 10 to 15 wt.% in the conversion of EB to styrene can be achieved compared to the two reactor process. In a three reactor process the three reactors can all be the same size or they can vary in size. Preferably, the first reactor is about 50 to about 100 percent of the size of the second and third reactors which are typically the same size.

Among the additional benefits achieved by employing more than two dehydrogenation reaction stages in the conversion of ethylbenzene to styrene are the following: the first reactor can use a less active but more selective and physically stable catalyst compared to the catalyst used in the second and third reactors, the pressure drop increase rate of the second and third may be reduced with the first reactor acting as a "guard" reactor dampening the deleterious effects of utility upsets and the like.

Employing a multiple reactor system with more than two reactors with split-flow of the hydrocarbon feed to the first and second reactors as practiced by the process of the present invention, the preferred split-flow fraction of hydrocarbon feed sent to the ι reactor is between about 0.6 and about 0.95. A more preferred fraction of hydrocarbon feed sent to the first reactor is between about 0.7 and about 0.9. Above a fraction of about 0.95, benefits obtained from the present process are minimized because the steam to hydrocarbon weight ratio can not be significantly different in the first reactor than it is in the other reactors of the process. Below a fraction of about 0.6 the benefits of employing an additional reactor are lost because a significant part of the hydrocarbon feed bypasses the catalyst of the first reactor. The remaining minor fraction of about 0.05 to about 0.4 of hydrocarbon feed containing a small amount of steam is introduced to the second reactor after having been combined with the reaction product of the first reactor.

The overall steam to hydrocarbon weight ratio (SHCR) is preferably in the range of about 1.2 to about 3.0. More preferably, the SHCR is about 1.3 to about 2.5 and most preferably the range of the SHCR is about 1.5 to about 2.0. A small amount of steam of about 0.1 to about 0.4 pounds of steam per pound of hydrocarbon is admixed with fresh ethylbenzene and recycle ethylbenzene before being preheated in a heat exchanger to 480–560° C. to minimize coking. All of the high temperature steam having a temperature of 760° C. or greater is added to a major fraction of the admixture of ethylbenzene and steam before being introduced to the first reaction stage.

The catalysts employed for the dehydrogenation reactors of this invention are those containing an oxide of iron. Preferably, a substantial portion of such iron oxide is in the form $Fe_3O_4$, although $Fe_2O_3$ may be reduced in situ by hydrogen to $Fe_3O_4$. Usually, further reduction to FeO leads to an inactive catalyst species. Other materials can be present in minor amounts as promoters or stabilizers. Examples of such materials are nonoxidation catalytic compounds of Groups IA, IB, IIA, IIB, IIIA, VB, VIB, VIIB and rare earths, such as zinc oxide, magnesium oxide, chromium or copper salts, potassium oxide, potassium carbonate, oxides of chromium, manganese, aluminum, vanadium, thorium and molybdenum. For example, an iron oxide catalyst useful in the process of this invention may contain about 50 to about 95 wt.% iron oxide measured as $Fe_2O_3$, about 5 to about 30 wt.% potassium compound, measured as potassium oxide, such as potassium carbonate and potassium oxide, and up to 20 wt.% of other compounds, measured as their oxides, such as compounds of vanadium, cadmium, magnesium, manganese, nickel, rare earths, chromium, and mixtures thereof. Preferable iron oxide-containing catalysts contain about 70 to about 90 wt.% iron oxide (as $Fe_2O_3$), about 5 to about 30 wt.% potassium compound (as $K_2O$) and up to 20 wt.% other compounds measured as their oxides. One specific example of an iron-oxide containing catalyst suitable for the ethylbenzene dehydrogenation of this invention contains about 80–90 wt.% iron oxide (as $Fe_2)_3$), about 8–15 wt.% potassium oxide, about 1—3 wt.% chromium oxide and about 0—1 wt.% vanadium oxide. While these known commercial dehydrogenation catalysts are preferred, other known catalysts may be used, including those comprising ferrous oxide-potassium oxide, other metal oxides and/or sulfides, including those of calcium, lithium, strontium, magnesium, beryllium, zirconium, tungsten, molybdenum, titanium, hafnium, vanadium, aluminum, chromium, copper, and mixtures of two or more including chromia-alumina, alumina-titania, alumina-vanadia, etc. Similarly, the various methods of preparing the aforesaid catalyst are well known within the prior art.

The amount of catalyst contained in each catalyst bed may be varied considerably. Usually, the amount of catalyst is expressed in terms of bed depth which may range from 6 inches to 50–60 feet, depending upon such conditions as alkylated aromatic hydrocarbon feed rate and the amount of heat which therefore must be added to effectuate the reaction at an economical rate. Typically, the bed depth may range from 2 feet to 6 feet.

The reactor pressure may also be varied over a considerable range. Preferably, subatmospheric pressure is used although, in some cases, atmospheric or superatmospheric pressure may be desirable. Sufficient pressure must be maintained at the reactor inlet to overcome the pressure drop through the multi-beds of catalyst contained in the reactor vessels or in separate vessels if each such bed is contained in a separate reactor. Either multiple beds contained in a single reactor, or single beds in multiple reactors, or a mixture of these arrangements, may be used in the practice of this invention.

In a process to catalytically dehydrogenate ethylbenzene to styrene comprising reacting a feed comprising a mixture of ethylbenzene and steam in multiple reactors of the present invention the process conditions are a temperature of about 400° to about 800° C., a pressure of about 5 to about 300 kPa and a liquid hourly space velocity of about 0.05 to about 2 $hr^{-1}$. The streams which are introduced to each of the three reactors, the first admixture, the second admixture and the second reactor product are each heated to a temperature of about 590° to about 760° C. by conventional heat exchange means.

One embodiment of the improved process of the present invention for producing styrene in high concentration via a multistage vapor phase dehydrogenation of ethylbenzene under vacuum is shown in FIG. 1.

A fresh stream 10 of ethylbenzene having a purity of 99.5 weight percent or greater is admixed with a recycle stream 12 of ethylbenzene having a composition of about 85 to about 98 weight percent ethylbenzene, minor amounts of styrene and toluene and a trace amount of benzene.

The admixture of fresh and recycle ethylbenzene is vaporized in a vaporizer 20 and admixed with a small amount of steam from stream 16 before being preheated to 480–560° C. in a heat exchanger (not shown). A fraction of the vaporized and preheated admixture is mixed with a stream 14 of high temperature (760° C. or greater) steam such that the feed stream containing a fraction of the admixture of fresh and recycle ethylbenzene and steam reaches a temperature from 593° C. to 760° C.

The heated feed stream is contacted with dehydrogenation catalyst contained in a first bed 42 of a reactor vessel 40 under conditions sufficient to convert at least 30% by weight of the ethylbenzene therein to styrene. The reaction product obtained in reactor 40 is mixed with the remaining minor fraction 32 of the admixture of fresh and recycle ethylbenzene and a small quantity of steam is passed through value 30 to form a second feed mixture in transfer line 34. The second feed mixture in line 34 is heated to a temperature of 593° to 760° C. in an exchanger (not shown).

The second feed mixture is contacted with dehydrogenation catalyst in a second bed 52 contained in a reactor vessel 50 under conditions sufficient to convert at least 15% by weight of the ethylbenzene present therein to styrene.

The reaction product of reactor 50 is heated to a temperature of 593° to 760° C. in a heat exchanger (not shown) and fed via transfer line 38 to contact a dehydrogenation catalyst in a third bed 62 of a reaction vessel 60.

The reaction product of reaction vessel 60 has an EB conversion in the range of about 65 to about 80 wt.% and the styrene selectivity is about 90 to about 97%. Various heat exchange vessels (not shown) are used to cool reaction product stream 36 to minimize polymerization of the styrene and to recover heat. The styrene is recovered in high concentration from the heat exchanged reactor product in styrene recovery system 26. The styrene recovery system typically contains distillation towers and the like to recover styrene in stream 28 at purity levels of up to 99.9 wt.% and to recycle the unconverted ethylbenzene back to the dehydrogenation process.

The following examples and comparative runs demonstrate but do not limit the invention disclosed herein.

EXAMPLE 1

Example 1 compares the operation of a two-stage dehydrogenation reaction system with a three-stage dehydrogenation system.

Comparative Two-stage Run

Dehydrogenation of ethylbenzene to styrene tests were performed in a pilot plant using two 1.94-inch inside diameter and 80-inch overall length tubular downflow reactors in series with five adiabatic heating zones along each reactor length. The reactor internal temperatures were measured using thermocouples placed in horizontal nozzles located along the reactor length. The hydrocarbon feed and liquid product samples were analyzed using Hewlett-Packard Model 5700A and 5890 gas chromatographs equipped with flame ionization detectors and the off-gas samples were analyzed using a Schimadzu 9A gas chromatograph equipped with flame ionization and thermal conductivity cells. A total batch of 2,900 $cm^3$ of United Catalyst Inc. G84C potassium-promoted iron-oxide containing dehydrogenation catalyst, in the form of ⅛-inch extrudates, was loaded equally into 30-inch midsections of the two reactors. The sections above and below the catalyst midsection in each of the reactors were filled with inert low surface area alpha-alumina spheres to support the catalyst and to facilitate a uniform mixing of the steam and hydrocarbon feed and a uniform heat distribution in the steam and hydrocarbon feed. The catalyst was steamed in situ for 18 hours at about 590° C. prior to introduction of hydrocarbon feed. Superheated steam was combined with a preheated hydrocarbon feedstream before being introduced into a preheat zone of the first reactor where the feed temperature was adjusted to a target operating condition before contacting the first catalyst bed. The hydrocarbon (HC) feedstream typically contained 97.9 wt.% ethylbenzene, 2 wt.% styrene and trace amounts of toluene and benzene. The effluent from the first reactor was reheated in the preheat zone of the second reactor prior to entering the second catalyst bed. The effluent from the second reactor was condensed in a product recovery section and separated into a hydrogen-rich off-gas stream, liquid hydrocarbon product stream and water. The off-gas stream was metered and analyzed for hydrogen, carbon oxides and $C_1$-$C_3$ light hydrocarbon content by gas chromatography. The liquid hydrocarbons were analyzed for benzene, toluene, ethylbenzene, styrene and other hydrocarbons boiling above styrene by gas chromatography.

Ethylbenzene (EB) conversion was measured at constant operating conditions with test conditions and EB conversions shown in Table I. The liquid hourly space velocity (LHSV) is defined as the volumetric liquid hydrocarbon feed rate (corrected to 15.6° C.) divided by the volume of catalyst charged into the first or second reactors. Catalyst bed inlet temperatures were 636° C. for the first reactor and 637° C. for the second reactor. Reactor pressures shown in Table I refer to the pressure at the inlet of the first catalyst bed and the outlet of the second catalyst bed. The percent EB conversion is the overall EB disappearance in the two reactor stages divided by the amount of EB in the feed-stream and multiplied by 100.

Three-stage Run

Dehydrogenation of ethylbenzene to styrene tests were performed in a pilot plant using three tubular downflow reactors in series having dimensions of 1.94-inch inside diameter and 80-inch overall length and constructed with five adiabatic heating zones along the reactor length. A total batch of 4,060 cm³ of United Catalyst Inc. G84C potassium-promoted iron-oxide containing dehydrogenation catalyst, in the form of ⅛-inch extrudates, was loaded into the three reactors. A total of 1,160 cm³ were loaded into a 24-inch length midsection of the first reactor and a loading of 1,450 cm³ was loaded into a 30-inch midsection of each of the second and the third reactors. The sections above and below the catalyst midsection in each of the reactors were filled with inert low surface area alpha-alumina spheres to support the catalyst and to facilitate a uniform mixing of the steam and hydrocarbon feed and a uniform heat distribution in the steam and hydrocarbon feed. After the catalyst was aged in the three reactors under ethylbenzene dehydrogenation conditions, a series of tests comparing the two-stage run with the three-stage run where the hydrocarbon feed was split to the first and second reactor were made. Based on a large number of two-stage and three-stage runs a computer model was developed to determine the effects of run conditions on styrene production rate. For a production rate of 742.1 grams/hr a two-stage pilot plant production run is presented in Table I and a split-flow three-stage pilot plant production run for the same production rate of 742.1 grams/hr is also presented in Table I.

TABLE I

| Comparison of Two-Stage vs. Three-Stage Operation | | |
|---|---|---|
| Example Identification | Two-stage | Three-stage |
| Catalyst age, months | 1.5 | 3.5 |
| Hydrocarbon (HC) feed rate, g/hr | 1310 | 1135 |
| Fraction of HC feed to R-1 | NA | 0.8 |
| R-1 LHSV, hr⁻¹ | NA | 0.9 |
| R-2 LHSV, hr⁻¹ | 1.04 | 0.9 |
| R-3 LHSV, hr⁻¹ | 1.04 | 0.9 |
| Reactor steam rate, g/hr | 2711 | 2349 |
| R-1 steam/HC weight ratio | NA | 2.59 |
| R-2 and R-3 steam/HC weight ratio | 2.07 | 2.07 |
| Reactor inlet temperature, °C. | | |
| R-1 | NA | 628 |
| R-2 | 636 | 636 |
| R-3 | 637 | 637 |
| Pressure, psia | | |
| R-1 inlet | NA | 24.1 |
| R-2 inlet | 22.2 | 21.2 |
| R-3 outlet | 17.7 | 17.7 |
| Overall Results | | |
| EB conversion, wt. % | 62.9 | 73.8 |
| Styrene selectivity, wt. % | 92.0 | 90.5 |
| Styrene production rate, g/hr | 742.1 | 742.1 |
| Styrene as wt. % of HC feed rate | 56.7 | 65.4 |

NA = Not Applicable

EXAMPLE 2

Dehydrogenation of ethylbenzene to styrene tests were performed in a pilot plant using three tubular downflow reactors in series. The reactors have the same dimensions of 1.94-inch inside diameter and 80-inch overall length and are constructed with five adiabatic heating zones along the reactor length. A total batch of 4,060 cm³ of United Catalyst Inc. G84C potassium-promoted iron-oxide containing dehydrogenation catalyst, in the form of ⅛-inch extrudates, was loaded into the three reactors. A total of 1,160 cm³ was loaded into a 24-inch length midsection of the first reactor and a loading of 1,450 cm³ was loaded into a 30-inch midsection of the second and the third reactors. The sections above and below the catalyst midsection in each of the reactors were filled with inert low surface area alpha-alumina spheres to support the catalyst and to facilitate a uniform mixing of the steam and hydrocarbon feed and a uniform heat distribution in the steam and hydrocarbon feed. After the catalyst was aged for 169 days in the three reactors under ethylbenzene dehydrogenation conditions, a series of tests comparing a full-flow of hydrocarbon feed to the first reactor mode of operation with a split-flow of hydrocarbon feed to the first and second reactor mode of operation were made.

Run A—Full-Flow

All of the ethylbenzene (EB) was introduced to the inlet of the first reactor at a rate of 1,740 cm³/hr. The liquid hourly space velocity (LHSV), defined as the volumetric liquid hydrocarbon feed rate divided by the volume of catalyst in the second or third reactor, for the run was 1.2 hr⁻¹. The inlet temperature of each of the three reactors was 632° C. The process steam required to provide heat for the endothermic dehydrogenation reaction was introduced to the first reactor. The steam to hydrocarbon weight ratio (SHCR) was maintained at a ratio of 2.0 for several days and then reduced to a ratio of 1.4. The first reactor inlet pressure was 20.1 psia and the third reactor outlet pressure was 9.8 psia. The overall EB conversion was 72.1 wt.% initially and the conversion decreased to 64.8 wt.% after nine days of testing representing a conversion loss rate of 0.8 wt.%/day. The first reactor EB conversion decreased from 33.2 wt.% to 30.3 wt.% during the nine day run. The styrene selectivity was 93.3 wt.%.

Run B—Split-Flow

After Run A, the SHCR was increased to 2.0 and the pilot plant was run at the conditions of Run A before operation was switched to split-flow feed of the hydrocarbon feed. For split-flow operation, 80 wt.% of the total EB feed of 1,740 cm³/hr was introduced to the inlet of the first reactor. The balance of the hydrocarbon feed, 20 wt. %, was introduced to the second reactor. LHSV based on the second or third reactor catalyst loading for the run was 1.2 hr$^1$. The inlet temperature of each of the three reactors was 632° C. The process steam was introduced to the first reactor. The SHCR was maintained at a ratio of 1.75 for the first reactor and was 1.4 for the second and third reactors. The first reactor inlet pressure was 20.1 psia and the third reactor outlet pressure was 9.8 psia. The overall EB conversion was 66.7 wt.% initially and decreased to 63.2 wt.% after nine days of testing representing a conversion loss rate of 0.4 wt.%/day. The first reactor EB conversion decreased from 35.3 wt.% to 34.9 wt.% during the nine day run. The styrene selectivity was 93.5 wt.

Run C—Full-Flow

After Run B, the operation was switched to full-flow without changing the other conditions of Run B. After one day, the overall EB conversion was 62.8 wt.%.

Data for Example 2 with an experimental run for full-flow of hydrocarbon feed to the R-1 reactor, an experimental run for the split-flow of hydrocarbon feed to the R-1 reactor and the R-2 reactor and another run for full-flow operation are given in following Table II.

TABLE II
Comparison of Full-Flow vs. Split-Flow Operation

| Run Identification | A | B | C |
|---|---|---|---|
| Days on stream: | 9 | 9 | 1 |
| Hydrocarbon (HC) feed rate, cm$^3$/hr | 1740 | 1740 | 1740 |
| Fraction of HC feed to R-1 | 1.0 | 0.8 | 1.0 |
| R-1 LHSV, hr$^{-1}$ | 1.50 | 1.20 | 1.50 |
| R-2 LHSV, hr$^{-1}$ | 1.20 | 1.20 | 1.20 |
| R-3 LHSV, hr$^{-1}$ | 1.20 | 1.20 | 1.20 |
| Reactor inlet temperature, °C. | | | |
| R-1 | 632 | 632 | 632 |
| R-2 | 632 | 632 | 632 |
| R-3 | 632 | 632 | 632 |
| Pressure, psia | | | |
| R-1 inlet | 20.1 | 20.1 | 20.1 |
| R-3 outlet | 9.8 | 9.8 | 9.8 |
| Overall Results | | | |
| Initial EB conversion, wt. % | 72.1 | 66.7 | 63.2 |
| End of Run EB conversion, wt. % | 64.8 | 63.2 | 62.8 |
| Styrene selectivity, wt % | 93.3 | 93.5 | — |

EXAMPLE 3

Dehydrogenation of ethylbenzene to styrene tests were performed in a pilot plant using a 0.75-inch inside diameter and 24-inch overall length tubular downflow reactor with a central-longitudinal thermowell. A total of 50 grams of United Catalyst Inc. G84C potassium-promoted iron-oxide containing dehydrogenation catalyst, in the form of 150-inch extrudates, was loaded into 6-inch midsection of the reactor. The sections above and below the catalyst midsection in each of the reactors were filled with inert low surface area alpha-alumina spheres to support the catalyst and to facilitate a uniform mixing of the steam and hydrocarbon feed and a uniform heat distribution in the steam and hydrocarbon feed. The 6-inch catalyst zone was heated by a heating jacket to maintain the catalyst bed isothermally at a temperature of 593° C. The reactor pressure was maintained at approximately 14.7 psia. Ethylbenzene was fed to the reactor at a 20 cc/hr to give an LHSV of 0.48 hr$^{-1}$. Various runs were made to illustrate the importance of the steam/hydrocarbon weight ratio in maintaining the catalyst performance as well as steam usage savings. These run conditions and results are given below and in Table III.

Run D—Split-flow with SHCR of 2.1

Run D was made to simulate a first stage of a three-stage system operating under a split-flow mode in which the first reactor steam/hydrocarbon weight ratio is 2.1 when 76% of the total hydrocarbon feed is directed to the first reactor and the SHCR for the second and third reactor is 1.6. Operating at these conditions, the EB conversion declined from 68.1% on day 12 of the experiment to 67.9% on day 19 for an EB conversion decline of 0.03 wt.%/day.

Run E—Full-flow with SHCR of 1.6

Run E was made to simulate the first stage of a three-stage system operating under a full-flow of hydrocarbon to the first reactor in which the SHCR was 1.6. A marked EB conversion decline rate of 1.0 wt. %/day was observed between day 20 and day 28 of the experiment.

Run F—SHCR of 2.0 and greater

Run F was run at various SHCR of 2.0 and greater to determine if the EB conversion loss of Run E could be recovered by increasing the SHCR. The higher SHCR had very little effect in increasing the EB conversion after the EB conversion decline obtained in the simulated full-flow operation of Run E.

TABLE III
Effect of Steam/Hydrocarbon Weight Ratio

| Run Identification | D | D | E | E |
|---|---|---|---|---|
| Reactor Conditions | | | | |
| Day on stream | 12 | 19 | 20 | 28 |
| LHSV, hr$^{-1}$ | 0.48 | 0.48 | 0.48 | 0.48 |
| Pressure, psia | 14.7 | 14.7 | 14.7 | 14.7 |
| Temperature, °C. | 593 | 593 | 593 | 593 |
| Steam/hydrocarbon weight ratio | 2.1 | 2.1 | 1.6 | 1.6 |
| Overall Results | | | | |
| EB conversion, wt. % | 68.1 | 67.9 | 64.8 | 56.8 |
| Styrene selectivity, wt. % | 92.4 | 92.5 | 92.3 | 92.3 |
| EB conversion decline (wt. %/day) | — | 0.03 | — | 1.0 |
| Run Identification | F | F | F | F |
| Reactor Conditions | | | | |
| Day on stream | 33 | 34 | 35 | 36 |
| LHSV, hr$^{-1}$ | 0.48 | 0.48 | 0.48 | 0.48 |
| Pressure, psia | 14.7 | 14.7 | 14.7 | 14.7 |
| Temperature, °C. | 593 | 593 | 593 | 593 |
| Steam/hydrocarbon weight ratio | 2.0 | 2.1 | 2.4 | 2.4 |
| Overall Results | | | | |
| EB conversion, wt. % | 63.7 | 64.0 | 65.5 | 65.7 |
| Styrene selectivity, wt. % | 92.4 | 92.4 | 92.2 | 92.6 |
| EB conversion decline (wt. %/day) | — | — | — | — |

We claim:

1. A process to catalytically dehydrogenate alkylated aromatic hydrocarbons to styrene in multiple reaction stages comprising:
    (a) admixing steam and a major weight fraction between about 0.6 and about 0.95 of a hydrocarbon feed stream to form a first admixture having a first reactor steam to hydrocarbon weight ratio in the range of about 1.26 to about 5.0;
    (b) contacting the first admixture with dehydrogenation catalyst in a first reaction stage under reaction conditions to form a first reaction product;

(c) admixing the first reaction product with a remaining minor weight fraction of the hydrocarbon feed stream to form a second admixture having a second reactor steam to hydrocarbon weight ratio in the range of about 1.2 to about 3.0 wherein said first reactor steam to hydrocarbon weight ratio is greater than said second reactor steam to hydrocarbon weight ratio;

(d) contacting the second admixture with dehydrogenation catalyst in a second reaction stage under reaction conditions to form a second reaction product;

(e) contacting the second reaction product with dehydrogenation catalyst in a third reaction stage under reaction conditions to form a third reaction product; and (f) processing the third reaction product in a recovery system to recover the styrene and to recycle a recycle stream comprising unconverted ethylbenzene.

2. The process according to claim 1 wherein said major weight fraction is between about 0.7 and about 0.9.

3. The process according to claim 1 wherein the reaction conditions of steps (b), (d) and (e) are a temperature of about 400° to about 800° C., a pressure of about 5 to about 300 kPa and a liquid hourly space velocity of about 0.05 to about 2 hr$^{-1}$.

4. The process according to claim 3 wherein the first admixture, the second admixture and the second reaction product are each heated to a temperature of about 590° to about 760° C.

5. The process according to claim wherein said hydrocarbon feed stream comprises ethylbenzene.

6. The process according to claim 5 wherein said hydrocarbon feed stream contains about 0.1 to about 0.4 pounds of steam per pound of hydrocarbon.

7. The process according to claim 5 wherein said hydrocarbon feed stream comprises a fresh ethylbenzene stream having greater than 99.5 wt.% ethylbenzene and a recycle stream having about 85 to about 98 wt.% ethylbenzene.

8. The process according to claim 1 wherein the second reactor steam to hydrocarbon weight ratio is about 1.3 to about 2.5.

9. The process according to claim wherein the second reactor steam to hydrocarbon weight ratio is about 1.5 to about 2.0.

10. The process according to claim 1 wherein the recycle stream comprises about 85 to about 98 wt.% ethylbenzene.

11. An improved multistage ethylbenzene dehydrogenation process comprising:
(a) admixing steam and a weight fraction between about 0.7 and about 0.9 of a hydrocarbon feed stream comprising ethylbenzene at a first reactor steam to hydrocarbon weight ratio between about 1.67 to about 2.85 to form a first admixture;
(b) contacting the first admixture with dehydrogenation catalyst in a first dehydrogenation reactor under reaction conditions to form a first reaction product;
admixing the first reaction product with a remaining weight fraction between about 0.1 and about 0.3 of the hydrocarbon feed stream to form a second admixture; and
(d) introducing the second admixture to a second dehydrogenation reactor wherein the first reactor steam to hydrocarbon weight ratio is greater than a second reactor steam to hydrocarbon weight ratio.

12. The process according to claim 11 wherein said reaction conditions are a temperature of about 400° to about 800° C., a pressure of about 5 to about 300 kPa and a liquid hourly space velocity of about 0.05 to about 2 hr$^{-1}$.

13. The process according to claim 11 wherein said second reactor steam is hydrocarbon weight ratio is about 1.5 to about 2.0.

14. The process according to claim 11 wherein said hydrocarbon feed stream contains about 0.1 to about 0.4 pounds of steam per pound of hydrocarbon.

15. The process according to claim 11 wherein said hydrocarbon feed stream comprises a fresh ethylbenzene stream having greater than 99.5 wt.% ethylbenzene and a recycle ethylbenzene stream having about 85 to about 98 wt.% ethylbenzene.

16. In a process to catalytically dehydrogenate ethylbenzene to styrene comprising reacting a mixture of ethylbenzene and steam in multiple reactors at a temperature of about 400° to about 800° C., a pressure of about 5 to about 300 kPa and at a liquid hourly space velocity of about 0.05 to about 2 hr$^{-1}$, the improvement comprising: feeding steam and a major weight fraction of an ethylbenzene feed stream to a first reactor and feeding a remaining minor fraction of the ethylbenzene feed stream and product of the first reactor to a second reactor wherein the steam to hydrocarbon weight ratio in the first reactor is greater than the steam to hydrocarbon weight ratio in the second reactor.

* * * * *